(12) United States Patent
Gruber

(10) Patent No.: US 9,161,810 B2
(45) Date of Patent: Oct. 20, 2015

(54) METHODS, COMPOSITIONS AND APPARATUSES FOR FACILITATING REGENERATION

(75) Inventor: Lewis Gruber, Chicago, IL (US)

(73) Assignee: Siwa Corporation, Chicago, IL (US)

(\*) Notice: Subject to any disclaimer, the term of this patent is extended or adjusted under 35 U.S.C. 154(b) by 817 days.

(21) Appl. No.: 13/332,976

(22) Filed: Dec. 21, 2011

(65) Prior Publication Data

US 2012/0183534 A1    Jul. 19, 2012

Related U.S. Application Data

(63) Continuation of application No. 12/994,421, filed as application No. PCT/US2009/044951 on May 22, 2009.

(60) Provisional application No. 61/055,846, filed on May 23, 2008.

(51) Int. Cl.
| A61K 39/395 | (2006.01) |
| A61B 18/18 | (2006.01) |
| A61B 18/20 | (2006.01) |
| A61B 18/00 | (2006.01) |
| A61N 5/10 | (2006.01) |
| A61N 7/02 | (2006.01) |

(52) U.S. Cl.
CPC .......... *A61B 18/18* (2013.01); *A61B 18/1815* (2013.01); *A61B 18/20* (2013.01); *A61B 2018/0047* (2013.01); *A61K 39/395* (2013.01); *A61N 5/10* (2013.01); *A61N 7/02* (2013.01)

(58) Field of Classification Search
None
See application file for complete search history.

(56) References Cited

U.S. PATENT DOCUMENTS

| 4,217,344 A | | 8/1980 | Vanlerberghe et al. |
| 4,900,747 A | | 2/1990 | Vlassara et al. |
| 4,911,928 A | | 3/1990 | Wallach |
| 4,917,951 A | | 4/1990 | Wallach |
| 5,494,791 A | * | 2/1996 | Cohen ............................ 435/7.9 |
| 5,518,720 A | * | 5/1996 | Cohen ........................ 424/137.1 |
| 5,601,526 A | | 2/1997 | Chapelon et al. |
| 5,693,762 A | * | 12/1997 | Queen et al. ................ 530/387.3 |
| 5,702,704 A | * | 12/1997 | Bucala ........................ 424/137.1 |
| 5,766,590 A | * | 6/1998 | Founds et al. .............. 424/137.1 |
| 5,811,075 A | | 9/1998 | Vlassara et al. |
| 5,817,771 A | | 10/1998 | Bayley et al. |
| 5,984,882 A | | 11/1999 | Rosenschein et al. |
| 6,067,859 A | | 5/2000 | Kas et al. |
| 6,090,382 A | | 7/2000 | Salfeld et al. |
| 6,176,842 B1 | | 1/2001 | Tachibana et al. |
| 6,245,318 B1 | | 6/2001 | Klibanov et al. |
| 6,309,355 B1 | | 10/2001 | Cain et al. |
| 6,380,165 B1 | * | 4/2002 | Al-Abed et al. ........... 548/300.1 |
| 6,387,373 B1 | | 5/2002 | Wright et al. |
| 6,670,136 B2 | | 12/2003 | Schmidt et al. |
| 6,676,963 B1 | | 1/2004 | Lanza et al. |
| 6,818,215 B2 | | 11/2004 | Smith et al. |
| 6,821,274 B2 | | 11/2004 | McHale et al. |
| 7,033,574 B1 | | 4/2006 | Schneider et al. |
| 7,101,838 B2 | | 9/2006 | Stern et al. |
| 7,256,273 B2 | | 8/2007 | Basi et al. |
| 7,347,855 B2 | | 3/2008 | Eshel et al. |
| 7,358,226 B2 | | 4/2008 | Dayton et al. |
| 7,367,988 B1 | | 5/2008 | Litovitz |
| 7,751,057 B2 | | 7/2010 | Oldenburg et al. |
| 7,815,570 B2 | | 10/2010 | Eshel et al. |
| 8,343,420 B2 | | 1/2013 | Cioanta et al. |
| 8,721,571 B2 | | 5/2014 | Gruber |
| 2002/0193784 A1 | | 12/2002 | McHale et al. |
| 2003/0073138 A1 | * | 4/2003 | Kientsch-Engel et al. .... 435/7.9 |
| 2003/0170173 A1 | | 9/2003 | Klaveness et al. |
| 2003/0229283 A1 | | 12/2003 | Craig et al. |
| 2004/0039416 A1 | | 2/2004 | Myhr |
| 2004/0141922 A1 | | 7/2004 | Klaveness et al. |
| 2004/0208826 A1 | | 10/2004 | Schneider et al. |
| 2004/0229830 A1 | | 11/2004 | Tachibana et al. |
| 2005/0084538 A1 | | 4/2005 | Dayton et al. |
| 2005/0283098 A1 | | 12/2005 | Conston et al. |
| 2006/0078501 A1 | | 4/2006 | Goertz et al. |
| 2006/0122543 A1 | | 6/2006 | Mayer et al. |
| 2006/0188883 A1 | | 8/2006 | Murray et al. |
| 2007/0059247 A1 | | 3/2007 | Lindner et al. |
| 2007/0065415 A1 | | 3/2007 | Kleinsek et al. |
| 2007/0083120 A1 | | 4/2007 | Cain et al. |
| 2007/0128117 A1 | | 6/2007 | Bettinger et al. |
| 2007/0129633 A1 | | 6/2007 | Lee et al. |

(Continued)

FOREIGN PATENT DOCUMENTS

| AU | 2009/248945 | 5/2014 |
| WO | 96/20958 | 7/1996 |

(Continued)

OTHER PUBLICATIONS

Shibayama et al., Diabetes. Sep. 1999;48(9):1842-9.*
Vidarsson et al., Front. Immunol., Oct. 20, 2014 | doi: 10.3389/fimmu.2014.00520.*
Lin et al., Philos Trans R Soc Lond B Biol Sci. Jan. 5, 2013;368(1609):20110334. doi: 10.1098/rstb.2011.0334.*
Wautier, J-L. et al., "Protein Glycation: A firm link to endothelial cell dysfunction", Circulation Research, Journal of the American Heart Association, vol. 95, pp. 233-238, (2004).

(Continued)

*Primary Examiner* — Michael Szperka
(74) *Attorney, Agent, or Firm* — Evan Law Group LLC

(57) ABSTRACT

Apparatuses, compositions and methods for removing cells which interfere with regenerative processes. The apparatuses, compositions and methods selectively kill partially functional and/or non-functional cells versus functional cells while protecting functional proliferative cells to the extent that, upon removal of the killed cells by disintegration or scavenging, functional cells replace the partially- or non-functional cells.

12 Claims, 1 Drawing Sheet

(56) References Cited

U.S. PATENT DOCUMENTS

| | | | |
|---|---|---|---|
| 2008/0019986 | A1 | 1/2008 | Stern et al. |
| 2008/0051680 | A1 | 2/2008 | Luebcke |
| 2008/0063603 | A1 | 3/2008 | Schneider et al. |
| 2008/0139942 | A1 | 6/2008 | Gaud et al. |
| 2008/0160506 | A1 | 7/2008 | Liu et al. |
| 2009/0076390 | A1 | 3/2009 | Lee et al. |
| 2009/0306552 | A1 | 12/2009 | Furuzono et al. |
| 2010/0028359 | A1 | 2/2010 | Gu et al. |
| 2010/0226932 | A1 | 9/2010 | Smith et al. |
| 2011/0105961 | A1 | 5/2011 | Gruber |
| 2012/0130287 | A1 | 5/2012 | Gruber |
| 2013/0243785 | A1 | 9/2013 | Gruber |
| 2014/0303526 | A1 | 10/2014 | Gruber |

FOREIGN PATENT DOCUMENTS

| | | | |
|---|---|---|---|
| WO | WO 9620958 A1 * | 7/1996 | |
| WO | 97/49429 | 12/1997 | |
| WO | WO 9749429 A1 * | 12/1997 | |
| WO | 99/64463 | 12/1999 | |
| WO | 2009/143411 | 11/2009 | |
| WO | 2012/047629 | 4/2012 | |
| WO | 2012/071269 | 5/2012 | |
| WO | 2012/135616 | 10/2012 | |

OTHER PUBLICATIONS

International Search Report dated Jun. 27, 2012 for PCT application No. PCT/US2012/031446.
Immuno, Catalog No. 637061, 637062, "Mouse, anti-age (advanced glycation end products), monoclonal antibody", http://www.mpbio.com/detailed_info.php?family_key=0863706, 2 pages, accessed Jul. 26, 2012.
Ahmed, E. K. et al., "Protein modification and replicative senescence of WI-38 human embryonic fibroblasts", Aging Cell, vol. 9, pp. 252-272, (2010).
Vlassara, H. et al, "Advanced glycosylation endproducts on erythrocyte cell surface induce receptor-mediated phagocytosis by macrophages", J. Exp. Med., The Rockefeller University Press, vol. 166, pp. 539-549, (1987).
Yang, Z. et al., "Two novel rat liver membrane proteins that bind advanced glycosylation endproducts: Relationship to macrophage receptor for glucose-modified proteins", J. Exp. Med., The Rockefeller University Press, vol. 174, pp. 515-524, (1991).
Vlassara, H. et al, "Advanced glycation endproducts promote adhesion molecule (VCAM-1, ICAM-1) expression and atheroma formation in normal rabbits", Molecular Medicine, vol. 1, No. 4, pp. 447-456, (1995).
Vaysse, J. et al., "Adhesion and erthrophagocytosis of human senescent erthrocytes by autologous monocytes and their inhibition by β-galactosyl derivatives", Proc. Natl. Acad. Sci. USA, Cell Biology, vol. 83, pp. 1339-1343, (1986).
Li, Y. M. et al., "Prevention of cardiovascular and renal pathology of aging by the advanced glycation inhibitor aminoguanidine", Proc. Natl. Acad. Sci. USA, Medical Sciences, vol. 93, pp. 3902-3907, (1996).
Manesso, E. et al., "Dynamics of β-cell turnover: evidence for β-cell turnover and regeneration from sources of β-cells other than β-cell replication in the HIP rat", American Journal of Physiology—Endocrinology and Metabolism, vol. 297, pp. E323-E330, (2009).
Stepanov, A.V. et al., "Design of targeted B cell killing agents", PLoS One, vol. 6, issue 6, e20991, pp. 1-10, (2011).
Fact Sheet, "Targeted Cancer Therapies", www.cancer.gov/cancertopics/factsheet/Therapy/Fs7_49.pdf, pp. 1-8, (2012).
Kay, M.M. "Generation of senescent cell antigen on old cells initiates IgG binding to a neoantigen", Cellular and Molecular Biology (Noisy-le-Grand, France), vol. 39, No. 2, pp. 131-153, (1993), Abstract Only.
Dominaitiene, R. et al., "Effects of differently oxidized LDL on the expression of pro-inflammatory molecules in human monocytes in vitro", In Vitro and Molecular Toxicology, vol. 14, No. 2, pp. 83-97, (2001).
Dziarski, R., "Cell-bound albumin is the 70-kDa peptidoglycan-, lipopolysaccharide-, and lipoteichoic acid-binding protein on lymphocytes and macrophages", The Journal of Biological Chemistry, vol. 269, No. 32, pp. 20431-20436, (1994).
Peters Jr. T.,"5-Metabolism: Albumin in the body", All About Albumin Biochemistry, Genetics, and Medical Applications, Chapter 5, pp. 188-250, (1995).
Vlassara, H. et al., "High-affinity-receptor-mediated uptake and degradation of glucose-modified proteins: A potential mechanism for the removal of senescent macromolecules", Proceeding of the National Academy of Science, USA, Biochemistry, vol. 82, pp. 5588-5592, (1985).
Saltykov, B.B., "Mechanisms of development of diabetic macroangiopathy", Arkh Patol., vol. 63, No. 2, pp. 21-26, (2001), Abstract Only.
Grossin, N. et al., "Red blood cell adhesion in diabetes mellitus is mediated by advanced glycation end product receptor and is modulated by nitric oxide", Biorheology, vol. 46, No. 1, pp. 63-72, (2009).
Liang, Y. et al., "Rituximab for children with immune thrombocytopenia: A systematic review", PLoS One, vol. 7, issue 1, pp. 1-11, (2012).
Fehrenbach, H. et al., "Up-regulated expression of the receptor for advanced glycation end products in cultured rat hepatic stellate cells during transdifferentiation to myofibroblasts", Hepatology, vol. 34, No. 5, pp. 943-952, (2001).
Wade, N., "Purging cells in mice is found to combat aging ills", New York Times, found at NYTimes.com, pp. 1-3, (2011).
Roll, P. et al., "Anti-CD20 therapy in patients with rheumatoid arthritis", Arthritis & Rheumatism, vol. 58, No. 6, pp. 1566-1575, (2008).
Kajstura J. et al., "Myocyte turnover in the aging human heart", Circulation Research, vol. 107, pp. 1374-1386, (2010).
Baker, D.J. et al., "Clearance of p16Ink4a-positive senescent cells delays ageing-associated disorders", Nature, vol. 479, pp. 232-236, (2011).
Breyer, V. et al., "Intracellular glycation of nuclear DNA, mitochondrial DNA, and cytosolic proteins during senescence-like growth arrest", DNA Cell Biology, vol. 30, No. 9, pp. 681-689, (2011).
Ravelojaona, V. et al., "Expression of senescence-associated beta-galactosidase (SA-beta-Gal) by human skin fibroblasts, effect of advanced glycation end-products and fucose or rhamnose-rich polysaccharides", Archives of Gerontology and Geriatrics, vol. 48, issue 2, pp. 151-154, (2009).
de Groot, K. et al., "Vascular endothelial damage and repair in antineutrophil cytoplasmic antibody—associated vasculitis", Arthristis & Rheumatism, vol. 56, No. 11, pp. 3847-3853, (2007).
Imani, F. et al., "Advanced glycosylation endproduct-specific receptors on human and rat t-lymphocytes mediate synthesis of interferon y: role in tissue remodeling", J. Exp. Med., vol. 178, pp. 2165-2172, (1993).
Kirstein, M. et al., "Receptor-specific induction of insulin-like growth factor I in human monocytes by advanced glycosylation end product-modified proteins", J. Clin. Invest., vol. 90, pp. 439-446, (1992).
Le Grand, F. et al., "Skeletal muscle satellite cells and adult myogenesis", Curr. Opin. Cell Biology, vol. 19, No. 6, pp. 628-633, (2007).
Sasaki, M. et al., "Mesenchymal stem cells are recruited into wounded skin and contribute to wound repair by transdifferentiation into multiple skin cell type", The Journal of Immunology, vol. 180, pp. 2581-2587, (2008).
Agostini, A. et al., "Targeted cargo delivery in senescent cells using capped mesoporous silica nanoparticles", Angewandte Chemie International Edition, vol. 51, pp. 10556-10560, (2012).
Larson, R.A. et al., "Tumor lysis syndrome: Definition, pathogenesis, clinical manifestations, etiology and risk factors", found at www.uptodate.com/contents/tumor-lysis-syndrome-definition-pathogenesis-clinical-manifestations-etiology-and-risk-factors?detectedLanguage=en&source=search_result&search=tumor+lysis+syndrome&selectedTitle=2~69&provider=noProvider, pp. 1-4, printed on Jun. 11, 2013.
Hansel, T.T. et al., "The safety and side effects of monoclonal antibodies", Nature Reviews, vol. 9, pp. 325-337, (2010).

(56) References Cited

OTHER PUBLICATIONS

Nass, N. et al., "Advanced glycation end products, diabetes and ageing", Zeitschrift fur Gerontologie and Geriatrie, vol. 40, issue 5, pp. 349-356, (2007).
Shcheglova, T. et al., "Reactive immunization suppresses advanced glycation and mitigates diabetic nephropathy", Journal of the American Society of Nephrology, vol. 20, No. 5, pp. 1012-1019, (2009).
Meuter, A. et al., "Markers of cellular senescence are elevated in murine blastocysts cultured in vitro: molecular consequences of culture in atmospheric oxygen", Journal of Assisted Reproduction and Genetics, vol. 31, issue 10, pp. 1259-1267, (2014).
Freund, A. et al., "Inflammatory networks during cellular senescence: causes and consequences", Trends in Molecular Medicine, vol. 16, No. 5, pp. 238-246, (2010).
Hadrabová, J. et al., "Chicken immunoglobulins for prophylaxis: Effect of inhaled antibodies on inflammatory parameters in rat airways", Journal of Applied Biomedicine, 4 pages, Available online May 5, 2014.
Ferraccioli, G. et al., "Interleukin-1β and Interleukin-6 in arthritis animal models: Roles in the early phase of transition from acute to chronic inflammation and relevance for human rheumatoid arthritis", Molecular Medicine, vol. 16, issue 11-12, pp. 552-557, (2010).
Zhao, Y. et al., "The bovine antibody repertoire", Developmental & Comparative Immunology, vol. 30, issues 1-2, pp. 175-186, (2006).
Wagner, B. et al., "The complete map of the Ig heavy chain constant gene region reveals evidence for seven IgG isotypes and for IgD in the horse", Journal of Immunology, vol. 173, No. 5, pp. 3230-3242, (2004).
Strietzel, C.J. et al., "In vitro functional characterization of feline IgGs", Veterinary Immunology and Immunopathology, vol. 158, issues 3-4, pp. 214-223, (2014).
Patel, M. et al., "Sequence of the dog immunoglobulin alpha and epsilon constant region genes", Immunogenetics, vol. 41, issue 5, pp. 282-286, (1995).
Maass, D.R. et al., "Alpaca (*Lama pacos*) as a convenient source of recombinant camelid heavy chain antibodies (VHHs)", Journal of Immunology Methods, vol. 324, issues 1-2, pp. 13-25, (2007).
European Search Report dated Sep. 12, 2014 for EP application No. EP14170802.4-1408.
Fessler, J. et al., "Senescent T cells promote bone loss in rheumatoid arthritis", Abstracts of the American College of Rheumatology/Association of Rheumatology Health Professionals, Annual Scientific Meeting, Washington DC, Nov. 9-14, 2012, Arthritis & Rheumatism, vol. 64, supplement 10, p. 2312, (2012) found at http://blackwellpublishing.com/acrmeeting/abstract.asp?MeetingID=789&id=103040.
Weyand, C.M. et al., Abstract of "T-cell aging in rheumatoid arthritis", Current Opinion in Rheumatology, vol. 26, No. 1, pp. 93-100, (2014) found at http://www.ncbi.nlm.nih.gov/m/pubmed/24296720/.
Dvergsten, J. et al., "Prevalence of functionally active, senescent T cells in juvenile idiopathic arthritis", Abstracts of the American College of Rheumatology/Association of Rheumatology Health Professionals, Annual Scientific Meeting, Philadelphia, Oct. 16-21, 2009, Arthritis & Rheumatism, vol. 60, supplement 10, p. 1313, (2009), found at http://blackwellpublishing.com/acrmeeting/abstract.asp?MeetingID=761&id=80937.
Definition of "Dissociation constant" printed from Wikipedia, the free encyclopedia on Sep. 17, 2014 found at http://en.wikipedia.org/wiki/Dissociation_constant.
Sigma-Aldrich product specification of "Nα,Nα-Bis(carboxymethyl)-L-lysine trifluoroacetate salt ≥95% (TLC)", found at http://sigmaaldrich.com/catalog/product/sigma/c3205?lang=en&region=US, printed on Sep. 17, 2014.
"Pulmatrix demonstrates iSPERSE capabilities for inhaled dry powder delivery of antibiotics and antibodies", data presented at Respiratory Drug Delivery 2012, 3 pages, printed on Sep. 4, 2014, found at http://businesswire.com/news/home/20120515005279/en/Pulmatrix-Demonstrates-iSPERSE-Capabilities-Inhaled-Dry-Powder#.VEgU4hauNbs.
Chan, A.C. et al., "Therapeutic antibodies for autoimmunity and inflammation", Nature Reviews Immunology, vol. 10, pp. 301-316, (2010).
Pradat, P.F. et al., "Abnormalities of satellite cells function in amyotrophic lateral sclerosis", Amyotrophic Lateral Sclerosis, vol. 12, No. 4, pp. 264-271, (2011).
Tchkonia, T. et al., "Cellular senescence and the senescent secretory phenotype: therapeutic opportunities", The Journal of Clinical Investigation, vol. 123, No. 3, pp. 966-972, (2013).
Kitada, K. et al., "Aldosterone induces p21-regulated apoptosis via increased synthesis and secretion of tumour necrosis factor-α in human proximal tubular cells", Clinical and Experimantal Pharmacology and Physiology, vol. 39, No. 10, pp. 858-863, (2012).
Definition of "TNF inhibitor", printed from Wikipedia, the free encyclopedia on Oct. 4, 2014, 4 pages, found at http://en.wikipedia.org/wiki/TNF_inhibitor?oldid=628250399.
Definition of "Etanercept", printed from Wikipedia, the free encyclopedia on Aug. 24, 2014, 6 pages, found at http://en.wikipedia.org/wiki/Etanercept?oldid=622648157.
AbbVie, Inc., "Humira adalimumab: Learn about Humira", found at https://www.humira.com/rheumatoid-arthritis, 7 pages, printed on Aug. 11, 2014.
AbbVie, Inc., "Medication Guide for Humira", found at https://www.humira.com/rheumatoid-arthritis, 9 pages, printed on Aug. 11, 2014.
AbbVie, Inc., "Humira: A biologic that targets and helps block TNF-alpha", found at https://www.humira.com/rheumatoid-arthritis/how-humira-works-for-ra, 8 pages, printed on Aug. 11, 2014.
AbbVie, Inc., "How Humira (adalimumab) works video transcript", found at https://www.humira.com/rheumatoid-arthritis/how-humira-works-video-transcript, 5 pages, printed on Aug. 11, 2014.
AbbVie, Inc., "Humira and methotrexate—a combination that has demonstrated results", found at https://www.humira.com/rheumatoid-arthritis/humira-and-methotrexate, 7 pages, printed on Aug. 11, 2014.
Madhur, M.S. et al., "Senescent T cells and hypertension: New ideas about old cells", Hypertension, vol. 62, pp. 13-15, (2013).
James, P.E. et al., "Vasorelaxation by red blood cells and impairment in diabetes: Reduced nitric oxide and oxygen delivery by glycated hemoglobin", Circulation Research, vol. 94, pp. 976-983, (2004).
Cirocchi, R. et al., "Meta-analysis of thyroidectomy with ultrasonic dissector versus conventional clamp and tie", World Journal of Surgical Oncology, vol. 8, No. 112, pp. 1-7, (2010).
Lingeman, J.E. et al., "Current perspective on adverse effects in shock wave lithotripsy", White Paper, American Urological Association Education and Research, found at www.auanet.org/content/guidelines-and-quality-care/clinical-guidelines/main-reports/whitepaper.pdf, 17 pages, (2009).
International Search Report dated Apr. 26, 2012 for PCT application No. PCT/US2011/053399.
International Search Report dated Jun. 13, 2012 for PCT application No. PCT/US2011/061387.
Wautier, J.-L. et al., "Advanced glycation end products (AGEs) on the surface of diabetic erythrocytes bind to the vessel wall via a specific receptor inducing oxidant stress in the vasculature: A link between surface-associated AGEs and diabetic complications", Proc. Natl. Acad. Sci. USA, vol. 91, No. 16, pp. 7742-7746, (1994).
Siegel, R. J., et al., "Ultrasonic plaque ablation: A new method for recanalization of partially or totally occluded arteries", Circulation, vol. 78, No. 6, pp. 1443-1448, (1988).
Misur, I. et al., "Advanced glycation endproducts in peripheral nerve in type 2 diabetes with neuropathy", Acta Diabetol, vol. 41, pp. 158-166, (2004).
International Search Report dated Jul. 21, 2009 for PCT application No. PCT/US2009/44951.
Lindsey, J.B. et al., "Receptor for advanced glycation end-products (RAGE) and soluble RAGE (sRAGE): Cardiovascular implications", Diabetes Vascular Disease Research, vol. 6, No. 1, pp. 7-14, (2009).
Ando, K. et al., "Membrane proteins of human erythrocytes are modified by advanced glycation end products during aging in the circulation", Biochemical and Biophysical Research Communications, vol. 258, pp. 123-127, (1999).

(56) References Cited

OTHER PUBLICATIONS

Jandeleit-Dahm, K. et al., "The AGE/RAGE axis in diabetes-accelerated atherosclerosis", Clinical and Experimental Pharmacology and Physiology, vol. 35, pp. 329-334, (2008).
Sakata, N. et al., "Immunohistochemical localization of different epitopes of advanced glycation end products in human atherosclerotic lesions", Atherosclerosis, vol. 141, pp. 61-75, (1998).
Karachalias, N. et al., "Accumulation of fructosyl-lysine and advanced glycation end products in the kidney, retina and peripheral nerve of streptozotocin-induced diabetic rats", Biochemical Society Transactions, vol. 31, pp. 1423-1425, (2003).
Aroian, R. et al., "Pore-forming toxins and cellular non-immune defenses (CNIDs)", Current Opinion in Microbiology, vol. 10, pp. 57-61, (2007).
Dobson, J., "A twist on tumour targeting", Nature Materials, vol. 9, pp. 95-96, (2010).
Gutensohn, K. et al., "Extracorporeal plateletpheresis induces the interaction of activated platelets with white blood cells", Vox Sanguinis, vol. 78, No. 2, pp. 101-105, (2000).
Horiuchi, S. et al., "Immunochemical approach to characterize advanced glycation end products of the maillard reaction", The Journal of Biological Chemistry, vol. 266, No. 12, pp. 7329-7332, (1991).
Soetanto, K. et al., "Fundamental examination of cattle red blood cells damage with ultrasound exposure microscopic system (UEMS)", Japanese Journal of Applied Physics, vol. 37, part 1, No. 5B, pp. 3070-3073, (1998).
Harja, E. et al., "Vascular and inflammatory stresses mediate atherosclerosis via RAGE and its ligands in apoE−/− mice", The Journal of Clinical Investigation, vol. 118, No. 1, pp. 183-194, (2008).
Carstensen, E.L. et al., "Lysis of erythrocytes by exposure to cw ultrasound", Ultrasound in Medicine and Biology, vol. 19, No. 2, pp. 147-165, (1993).
Miller, M.W. et al., "Comparative sensitivity of human erythrocytes and lymphocytes to sonolysis by 1-MHz ultrasound", Ultrasound in Medicine and Biology, vol. 23, No. 4, pp. 635-638, (1997).
Iwata, H. et al. "Effect of carbonyl compounds on red blood cells deformability", Biochemical and Biophysical Research Communications vol. 321, pp. 700-706, (2004).
Schmitt, A. et al., "The binding of advanced glycation end products to cell surfaces can be measured using bead-reconstituted cellular membrane proteins", Biochimica et Biophysica Acta, vol. 1768, pp. 1389-1399, (2007).
Self-Medlin, Y. et al., "Glucose promotes membrane cholesterol crystalline domain formation by lipid peroxidation", Biochimica et Biophysica Acta, vol. 1788, pp. 1398-1403, (2009).
Singh, N. et al., "The PPAP-γ activator, rosiglitazone, inhibits actin polymerisation in monocytes: involvement of Akt and intracellular calcium", Biochemical and Biophysical Research Communications, vol. 333, pp. 455-462, (2005).
Li, Y-M. et al., "Effects of high glucose on mesenchymal stem cell proliferation and differentiation", Biochemical and Biophysical Research Communications, vol. 363, pp. 209-215, (2007).
Takata, K. et al., "Endocytic uptake of nonenzymatically glycosylated proteins is mediated by a scavenger receptor for aldehyde-modified proteins", The Journal of Biological Chemistry, vol. 263, No. 29, pp. 14819-14825, (1988).
Mi, Y. et al., "Apoptosis in leukemia cells is accompanied by alterations in the levels and localization of nucleolin", Journal of Biological Chemistry, vol. 278, pp. 8572-8579, (2003).
Christian, S. et al., "Nucleolin expressed at the cell surface is a marker of endothelial cells in angiogenic blood vessels", Journal of Cell Biology, vol. 163, No. 4, pp. 871-878, (2003).
Loo, T.W. et al., "Identification of residues in the drug translocation pathway of the human multidrug resistance P-glycoprotein by arginine mutagenesis", Journal of Biological Chemistry, vol. 284, No. 36, pp. 24074-24087, (2009).
Brundin, P. et al., "Prion-like transmission of protein aggregates in neurodegenerative diseases", Nature Reviews Molecular Cell Biology, vol. 11, No. 4, pp. 301-307, (2010).
Perez, C. et al., "Translational control of the abundance of cytoplasmic poly(A) binding protein in human cytomegalovirus-infected cells", Journal of Virology, vol. 85, No. 1, pp. 156-164, (2011).
Persson, J. et al., "Interleukin-1beta and tumour necrosis factor-alpha impede neutral lipid turnover in macrophage-derived foam cells", BMC Immunology, vol. 9, No. 70, pp. 1-11, (2008).
Vergne, I. et al., "Cell biology of mycobacterium tubercolosis phagosome", Annu. Rev. Cell Dev. Biology, vol. 20, pp. 367-394, (2004).
Moskowitz, S.M. et al., "The role of *pseudomonas* lipopolysaccharide in cystic fibrosis airway Infection", Subcell Biochemistry, vol. 53, pp. 241-253, (2010).
Hall-Stoodley, L. et al., "Direct detection of bacterial biofilms on the middle-ear mucosa of children with chronic otitis media", JAMA, vol. 296, No. 2, pp. 202-211, (2006).
Franke-Fayard, B. et al., "Sequestration and tissue accumulation of human malaria parasites: Can we learn anything from rodent models of malaria?", PLoS Pathogens, vol. 6, issue 9, pp. 1-10, e1001032, (2010).
Zhang, S. et al., "Delineation of diverse macrophage activation programs in response to intracellular parasites and cytokines", PLoS Neglected Tropical Diseases, vol. 4, No. 3, e648 (2010).
Ma, Y. et al., "NS3 helicase domains involved in infectious intracellular hepatitis C virus particle assembly", Journal of Virology, vol. 82, No. 15, pp. 7624-7639, (2008).
Korant, B.D. et al., "Inhibition by zinc of rhinovirus protein cleavage: interaction of zinc with capsid polypeptides", Journal of Virology, vol. 18, No. 1, pp. 298-306, (1976).
Ameli, S. et al., "Effect of immunization with homologous LDL and oxidized LDL on early atherosclerosis in hypercholesterolemic rabbits", Arteriosclerosis, Thrombosis, and Vascular Biology, vol. 16, pp. 1074-1079, (1996).
Nilsson, J. et al., "Inflammation and immunity in diabetic vascular complications", Current Opinion in Lipidology, vol. 19, issue 5, pp. 519-524, (2008).
Schiopu, A. et al., "Recombinant antibodies to an oxidized low-density lipoprotein epitope induce rapid regression of atherosclerosis in apobec-1$^{-/-}$/low-density lipoprotein receptor$^{-/-}$ mice", Journal of the American College of Cardiology, vol. 50, No. 24, pp. 2313-2318, (2007).
Schiopu, A. et al., "Recombinant human antibodies against aldehyde-modified apolipoprotein B-100 peptide sequences inhibit atherosclerosis", Circulation, vol. 110, pp. 2047-2052, (2004).
Bassirat, M. et al., "Short- and long-term modulation of microvascular responses in streptozotocin-induced diabetic rats by glycosylated products", Journal of Diabetes and its Complications, vol. 24, pp. 64-72, (2010).
Ge, J. et al., "Advanced glycosylation end products might promote atherosclerosis through inducing the immune maturation of dendritic cells", Arteriosclerosis, Thrombosis, and Vascular Biology, vol. 25, pp. 2157-2163, (2005).
Gugliucci, A. et al., "Circulating advanced glycation peptides in streptozotocin-induced diabetic rats: evidence for preferential modification of IgG light chains", Life Sciences, vol. 62, No. 23, pp. 2141-2150, (1998).
Pullerits, R. et al., "Synovial fluid expression of autoantibodies specific for RAGE relates to less erosive course of rheumatoid arthritis", Rheumatology, vol. 46, pp. 1367-1371, (2007).
Bro, S. et al., "A neutralizing antibody against receptor for advanced glycation end products (RAGE) reduces atherosclerosis in uremic mice", Atherosclerosis, vol. 201, pp. 274-280, (2008).
Turk, Z. et al., "Detection of autoantibodies against advanced glycation endproducts and AGE-immune complexes in serum of patients with diabetes mellitus", Clinica Chimica Acta, vol. 303, pp. 105-115, (2001).
Li, M. et al., "Glycan changes: cancer metastasis and anti-cancer vaccines", Journal of Biosciences, vol. 35, No. 4, pp. 665-673, (2010).
Kyte, J.A. et al., "Third international conference on cancer vaccines/adjuvants/delivery for the next decade (CVADD 2009)", Expert Reviews Vaccines, vol. 9, No. 2, pp. 119-123, (2010).
Akbulut, H. et al., "Chemotherapy targeted to cancer tissue potentiates antigen-specific immune response induced by vaccine for in vivo

(56) References Cited

OTHER PUBLICATIONS antigen loading and activation of dendritic cells", Molecular Therapy, vol. 16, No. 10, pp. 1753-1760, (2008).
Li, Y.M. et al., "Glycation products in aged thioglycollate medium enhance the elicitation of peritoneal macrophages", Jounal of Immunological Methods, vol. 201, issue 2, pp. 183-188, (1997).
Poggioli, S. et al., "Age-related increase of protein glycation in peripheral blood lymphocytes is restricted to preferential target proteins", Experimental Gerontology, vol. 37, issue 10-11, pp. 1207-1215, (2002).
Poggioli, S. et al., "Evidence of preferential protein targets for age-related modifications in peripheral blood lymphocytes", Annals of the New York Academy of Sciences, vol. 1019, issue 1, pp. 211-214, (2004).
Jiang, Z-H. et al., "Synthetic vaccines: the role of adjuvants in immune targeting", Current Medicinal Chemistry, vol. 10, No. 15, pp. 1423-1439, (2003).
Buskas, T. et al., "Immunotherapy for cancer: Synthetic carbohydrate-based vaccines", Chemical Communications, Issue 36, pp. 5335-5349, (2009).
Cohen, M.P. et al., "Amelioration of diabetic nephropathy by treatment with monoclonal antibodies against glycated albumin", Kidney International, vol. 45, pp. 1673-1679, (1994).
Davis, P.J. et al., "How can thermal processing modify the antigenicity of proteins?", Allergy, vol. 56, supplemental 67, pp. 56-60, (2001).
Koga, M. et al. "Clinical impact of glycated albumin as another glycemic control marker", Endocrine Journal, vol. 57, No. 9, pp. 751-762, (2010).
Virella, G. et al., "Autoimmune response to advanced glycosylation end-products of human LDL", Journal of Lipid Research, vol. 44, pp. 487-493, (2003).
Ihssen, J. et al., "Production of glycoprotein vaccines in *Escherichia coli*", Microbial Cell Factories, vol. 9, No. 61, pp. 1-13, (2010).
Habets, K.L.L. et al., "Vaccination using oxidized low-density lipoprotein-pulsed dendritic cells reduces atherosclerosis in LDL receptor-deficient mice", Cardiovascular Research, vol. 85, pp. 622-630, (2010).
Mironova, R. et al., "Glycation and post-translational processing of human interferon-y expressed in *Escherichia coli*", The Journal of Biological Chemistry, vol. 278, No. 51, pp. 51068-51074, (2003).
Vogel, F.R. et al., "A compendium of vaccine adjuvants and excipients", Pharmaceutical Biotechnology, vol. 6, pp. 141-228, (1995).
Monograph series, World Health Organization, "Methods of Vaccine Production", part 4, chapters 18-29, pp. 189-267, (1973).
Cohen, M.P. et al., "Prevention of diabetic nephropathy in db/db mice with glycated albumin antagonists: A novel treatment strategy", The Journal of Clinical Investigation, vol. 95, pp. 2338-2345, (1995).
Naka, Y. et al., "RAGE Axis, Animal models and novel insights into the vascular complications of diabetes", Arteriosclerosis, Thrombosis, and Vascular Biology, vol. 24, pp. 1342-1349, (2004).
European Search Report dated Nov. 8, 2011 for PCT application No. PCT/US2009/044951.
Bierhaus, A. et al., "AGEs and their interaction with AGE-receptors in vascular disease and diabetes mellitus. I. the AGE concept", Cardiovascular Research, vol. 37, No. 3, pp. 586-600, (1998).
Murphy, J.F. "Trends in cancer immunotherapy", Clinical Medicine Insights: Oncology, vol. 4, pp. 67-80, (2010).
Beier, K.C., "Master switches of T-cell activation and differentiation", European Respiratory Journal, vol. 29, pp. 804-812, (2007).
Schmidlin, H., "New insights in the regulation of human B cell differentiation", Trends in Immunology, vol. 30, No. 6, pp. 277-285, (2009).

Coler, R.N. et al., "Development and characterization of synthetic glucopyranosyl lipid adjuvant system as a vaccine adjuvant", PLoS One, vol. 6, No. 1, e16333, pp. 1-12, (2011).
Cheadle, E.J., "Bugs as drugs for cancer", Immunology, vol. 107, pp. 10-19, (2002).
The Pink Book, Epidemiology and Prevention of vaccine preventable diseases, 11$^{th}$ Ed., pp. B7-B13, (2009), Found at www.cdc.gov/vaccines/pubs/pinkbook/downloads/appendices/b/excipient-table-1.pdf.
The Pink Book, Epidemiology and Prevention of vaccine preventable diseases, 11$^{th}$ Ed., 4 pages, (2009), Found at www.cdc.gov/vaccines/pubs/pinkbook/downloads/appendices/b/excipient-table-2.pdf.
Book Reviews, International Microbiology, vol. 7, pp. 291-295, (2004).
"Glycation: How eating sugar causes wrinkles", www.brighthub.com/health/diet-nutrition/articles/18410.aspx, 1 page, published Oct. 8, 2009.
Ellis, G., "The myth of the glycemic index and its child: good carbs-bad carbs", Targeted Body Systems, www.targetedbodysystems.com/tag/low-carb-diet-plans/, pp. 1-5, published Feb. 16, 2009.
"Diabetic glycation and inflammation—what diabetes does to your coronary arteries", www.rebelheartsurgeon-antioxidants.net/diabetic-glycation.html, pp. 1-9, downloaded Aug. 17, 2010.
Bumol, T.F. et al., "Monoclonal antibody and an antibody-toxin conjugate to a cell surface proteoglycan of melanoma cells suppress in vivo tumor growth", Proceeding of the National Academy of Science, vol. 80, pp. 529-533, (1983).
"AGEs (all species) antibody—Product Details", Antibodies Online, 4 pages, found at www.web.archive.org/web/20081229071154/http://www.antibodies-online.com/antibody/289931/AGEs+All+Species/, printed on Dec. 10, 2014.
"Antibody Engineering", Fusion Antibodies, 2 pages, found at www.web.archive.org/web/20080628225818/http://wwwv.fusionantibodies.com/index.cfm/area/information/page/engineering?, printed on Dec. 16, 2014.
Hargreaves, R.E.G. et al., "Selective depletion of activated T cells: the CD40L-specific antibody experience", TRENDS in Molecular Medicine, vol. 10, No. 3, pp. 130-135, (2004).
Leinenga, G. et al., "Scanning ultrasound removes amyloid-β and restores memory in an Alzheimer's disease mouse model", Science Translational Medicine, vol. 7, issue 278, pp. 1-11, (2015).
Peppa, M. et al., "Glucose, advanced glycation end products, and diabetes complications: What is new and what works", Clinical Diabetes, vol. 21, No. 4, pp. 186-187, (2003).
Lv, Y. et al., "Low-intensity ultrasound combined with 5-aminolevulinic acid administration in the treatment of human tongue squamous carcinoma", Cellular Physiology and Biochemistry, vol. 30, pp. 321-333, (2012).
Campisi, J. et al., "Cellular senescence: when bad things happen to good cells", Nature Reviews: Molecular Cell Biology, vol. 8, pp. 729-749, (2007).
"ALSUntangled No. 23: The Rife Machine and retroviruses", Amyotrophic Lateral Sclerosis and Frontotemporal Degeneration, vol. 15, pp. 157-159, (2014).
Roylance, D., "Mechanical properties of materials", pp. 1-128, (2008), available at www.web.mit.edu/course/3/3.225/book.pdf.
Waldmann, T.A., "Immunotherapy: past, present and future", Nature Medicine, vol. 9, No. 3, pp. 269-277, (2003).
Okamoto, T. et al., "Advanced glycation end products induce angiogenesis in vivo", Microvascular Research, vol. 63, pp. 186-195, (2002).
Nagai, R. et al., "Application of monoclonal antibody libraries for the measurement of glycation adducts", Biochemical Society Transactions, vol. 31, part 6, pp. 1438-1440, (2003).

\* cited by examiner

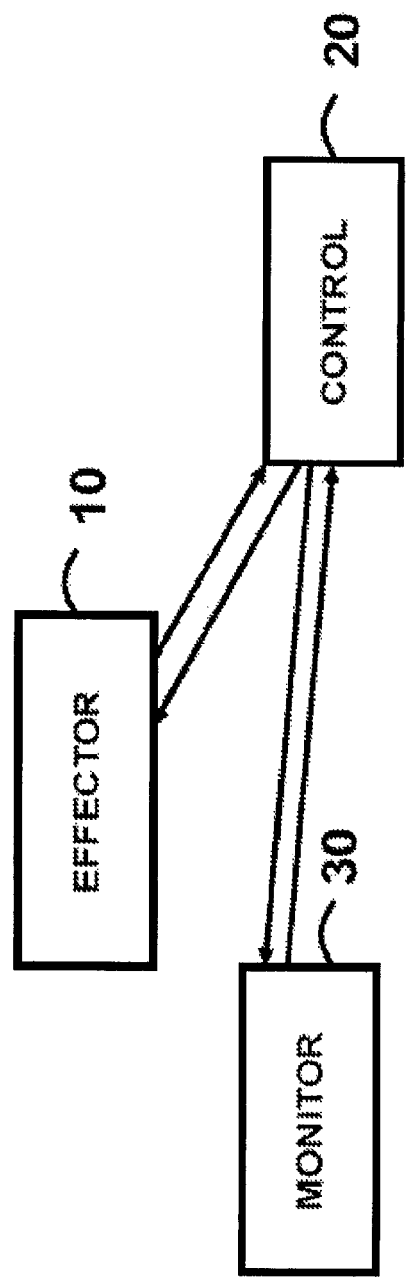

METHODS, COMPOSITIONS AND APPARATUSES FOR FACILITATING REGENERATION

CROSS-REFERENCE TO RELATED APPLICATION

This application is a continuation of U.S. application Ser. No. 12/994,421, METHODS, COMPOSITIONS AND APPARATUSES FOR FACILITATING REGENERATION, filed on Jan. 18, 2011. U.S. application Ser. No. 12/994,421 is the national phase of International Application No. PCT/US2009/044951, METHODS, COMPOSITIONS AND APPARATUS FOR FACILITATING REGENERATION, filed on May 22, 2009. International Application No. PCT/US2009/044951 claims the benefit of U.S. Provisional Application Ser. No. 61/055,846, METHODS, COMPOSITION AND APPARATUS FOR FACILITATING REGENERATION, filed on May 23, 2008, and is hereby incorporated in its entirety by reference.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISC

Not applicable.

FIELD OF THE INVENTION

The present invention relates in general to methods, compositions and apparatus for promoting tissue and organ regeneration, and in particular to preventing cells from inhibiting regenerative processes to obtain the recognized benefits in health and function associated with the results of regeneration.

BACKGROUND OF THE INVENTION

Tissue and organ regeneration research has focused on the need to stimulate regeneration by activating stem cells by soluble factors or treat partially- or non-functional cells to improve their function, e.g. by breaking damage-related crosslinks. Such research has overlooked the need to remove inhibitory effects.

Aging results from a combination of factors, but regeneration can overcome aging effects, if and to the extent that regenerative stem cells are functional. The stem cells, which replace cells, re-grow structures and renew the tissues of the body after normal wear-and-tear, give rise to replacement cells, and even structures, like hair follicles. In fact, if all stem cells in the body were destroyed, death would follow in a matter of days.

However, in a variety of diseases, malfunctions (such as male pattern baldness) and tissue injuries, cell types are not observed to be replaced when damaged or nonfunctional. Stem cell transplant therapy is proposed for such conditions, although it is not always successful.

The art has been left with the question as to why, then, does the body succumb to injury and aging when it has a mechanism for regeneration.

SUMMARY OF THE INVENTION

The present invention provides apparatus, compositions and methods for removing cells that interfere with regenerative processes by blocking locations in a tissue where progeny of stem cells can improve function. The present invention also reduces the proportion of partially- and non-functional cells without regard to location in a tissue.

Functionality according to the present invention is defined as the state of operation of a cell of the same type in a selected healthy individual.

The apparatuses, compositions and methods according to the present invention promote regenerative processes by differentially killing cells based inversely on the degree of functionality of the cells (i.e., the less functionality the more likely to be killed), and then applying that technique. This cell killing technique preferentially preserves proliferating cells. For example, any of lipofuscin, glycation end-products or cell stiffness can be selected as a proliferation-preserving marker of partial- or non-functionality. Cell killing technologies directed against such markers can include, respectively, lasers/intense light, antibodies, and ultrasound. Cells can be killed according to the present invention by physical, electromagnetic, chemical or biological techniques, for example. Physical techniques include without limitation ultrasound and other oscillatory methods for disrupting cell membranes or structures leading to cell death. Electromagnetic techniques include without limitation and as targeted by sensitizers (such as absorbent nanoparticles, for example) EMF (see, e.g., Litovitz, U.S. Pat. No. 7,367,988 for EMF methods), high intensity light, radio waves microwaves, lasers, magnetism and ionizing radiation. Chemical techniques include without limitation toxic nanoparticles, chemical toxins and structure removal compounds such as P-aminopropionitrile. Biological techniques include without limitation antibodies against partially-functional or non-functional cells and variations and modifications thereof, such as toxin conjugates and natural killer cells modified to express target-specific antibodies. Techniques can be combined as determined to be effective (e.g. see McHale et al., U.S. Pat. No. 6,821,274 for sensitization to ultrasound by EMF treatment). Apparatuses, methods and compositions according to the present invention can be used sequentially or simultaneously in combination as monitoring determines to be effective for promoting regeneration.

Preferably, the apparatuses, compositions and methods selectively kill partially and/or non-functional cells versus functional cells of the same cell type to the extent that, upon removal of the killed cells by disintegration or scavenging, functional cells replace them. The cell killing apparatus, compositions and methods according to the present invention must preferentially preserve proliferating, functional cells and must be of a degree that avoids excessive inflammatory responses.

Evaluation of improvement or maintenance of a desired result can be used to direct the frequency of reapplication of the apparatus, compositions and methods according to the present invention. The application and reapplication can be determined with the goal of gradual improvement to avoid overwhelming natural mechanisms, such as removal of cells/debris by scavenging cells.

BRIEF DESCRIPTION OF THE DRAWING

The FIGURE illustrates apparatus according to the present invention.

DETAILED DESCRIPTION

Higher multicellular organisms behave as communities of specialized cells that work together not to preserve each individual cell, but to preserve the organism as a whole. In humans during development, cells that are "in the way" of development are removed by programmed cell death, apoptosis, to benefit tissues, organs or the organism as a whole. Even when an organism reaches maturity, certain damaged cells, such as damaged blood cells are destroyed by the body to make way for replacements. The replacement cells are derived from stem cells. Accordingly, in a mature organism, cell turnover is the key to maintenance of a youthful/functional whole.

This turnover can come at the expense of destruction of functional cells to the extent that the destruction does not degrade the function of the organism over time. Thus, such destruction must preferentially target non-proliferating cells that are partially- or non-functional, but it need not absolutely avoid killing functional and proliferating cells. The goal is to preserve the community of cells (e.g. organism) not individual cells. Proliferating cells include both cells that are dividing and cells, such as stem cells, that divide normally when stimulated to do so.

While stem cells participate in mundane tissue replacement, injury can also be an occasion for release of a factor or factors to stimulate stem cell proliferation and differentiation. Stem cells give rise to cells which heal the injury, for example, healing a cut in an epithelium.

However, stem cell division and differentiation would be abnormal, even tumorigenic, in the presence of a normal complement of cells. Accordingly, there are mechanisms to prevent excessive proliferation. For example, the presence of a cell at a location in an epithelium prevents replacement at that position. An example of this sort of phenomenon is contact inhibition where cells cease proliferating when they come in contact with other cells. The phenomenon can be generalized to a rule that, to facilitate stem cell proliferation and differentiation for regeneration of cells at a location, there can not be a cell or structure at the location in the tissue.

In some cases, the human body includes cells for tearing down a structure, such as osteoclasts in bone, as well as cells for building up a structure, such as osteoblasts in bone. It is the balance between the activities of the two types of cells that determines the extent of the resulting structure. To the extent that any intrinsic mechanisms do not remove cells/structure for periodic renewal, the present invention provides for removal to promote regeneration.

The cell at the location that inhibits stem cell action can be fully functional, partially functional, or non-functional. Dead cells can be removed by scavenging macrophages, thus allowing for replacement, but a malfunctioning cell may remain despite deleterious effects on the subject (i.e., the organism of which they are a part). A partially or non-functional cell, i.e. a malfunctioning cell, can not be apoptotic, and, thus, can not stimulate clearance by macrophages on its own. Such malfunctioning cells are killed according to the present invention for removal by the body's natural processes.

Therapeutic killing of cells in cancer therapy is targeted against proliferating cells, the exact opposite of the present invention. According to the present invention, action against cancer is provided by stimulating proliferation of stem cells so that error-correcting mechanisms that function during cell division can correct mutations that otherwise might accumulate in a non-dividing cell.

Without limitation, partially or non-functional cells according to the present invention can fail to be fully functional due to damage, such as free radical damage, or cross-linkage as a result of reaction with sugars, i.e. glycation. Cells that are partially or non-functional due to a genetic makeup that is shared by stem cells of a subject can be replaced by exogenous stem cells having a fully functional genetic makeup.

Blocking stem cell action by a cell or structure at a location in a tissue interferes with the action of endogenous and transplanted stem cells. A structure that blocks stem cell action need not be a cell. Non-cellular material, such as scar tissue, can block such regeneration. This can explain failures in regeneration and in stem cell transplantation. To the extent feasible under a given situation, non-cellular blocking structures can be removed according to the present invention.

With removal of blocking cellular and/or non-cellular materials, appropriate regenerative cells, such as stem cells, are retained or supplemented by transplantation in order to permit regeneration. "Fully functional" is defined as the degree of a specified function for a particular cell type exhibited by an available progeny of a stem cell in a subject with or without stem cell transplantation, whichever is greater.

An example of an apparatus according to the present invention is illustrated in FIG. 1. Effector 10 is a device for killing cells. Effector 10 can be, without limitation, ultrasound equipment or a device for antibody administration, such as a drip apparatus. Control 20 is a device for regulating the operation of effector 10 according to preset parameters and/or as modified to ensure safety or effectiveness. Without limitation, control 20 can be a control panel of effector 10. Monitor 30 provides information regarding the degree of inflammatory response and/or other important factors in the condition of the subject to which effector 10 is applied. Information from monitor 30 can be used to adjust control 20 and thereby to adjust or change the operation of effector 10. Monitor 30 can be, without limitation, a thermometer connected to control 20.

A technique according to the present invention is selected to preferentially kill partially functional or nonfunctional cells or to remove non-cellular compositions, as opposed to indiscriminate killing, which has as great an effect on functional cells. A technique may be selected according to the present invention by exposing functional and partially functional and/or non-functional cells to the technique and choosing concentrations, intensities and characteristics such as wavelength, frequency, wave shape, continuity and treatment duration. The technique to be applied to a particular subject can be chosen on the basis of identifying an acceptable selectivity for partially functional and/or non-functional cells versus functional cells.

Suitable selection methods and criteria are readily available to those skilled in the art. Such selection methods are routinely applied by those of skill in the relevant arts to select laser treatment levels for removing blemishes, treating cancers by radiation therapy, selecting monoclonal antibodies, selecting toxins to be used therapeutically, and selecting ultrasound properties for therapy, for example. According to the present invention, selected techniques discriminate functional versus non-functional and/or partially functional cells of the same cell type as the functional cells.

Techniques that act upon differences between functional and partially or non-functional cells can be based upon cellular properties associated with dysfunction, such as cross-linking, membrane stiffness and brown coloration associated with lipofuscin in aged or senescent cells as opposed to nascent, dividing or functional cells. Techniques such as ultrasound, targeted to harmonic frequencies of cross-linked cell membranes or components, can be used according to the present invention. Likewise, techniques such as lasers or intense light of a wavelength preferentially absorbed by partially functional or non-functional cells can be used according to the present invention.

Techniques according to the present invention can be used to localize therapy where needed. Localization can be accomplished by, without limitation, computer assisted tomography, magnetic resonance imaging, and positron emission tomography. Most preferably, techniques according to the present invention can be applied to the whole organism without the need for localization.

Once techniques are chosen for one or more targets, the techniques can be applied periodically, particularly at a low intensity or concentration, to maintain or increase a positive balance between functional versus partially or non-functional cells. Gradual versus precipitate cell killing can aid in avoiding toxic effects from high levels of cellular breakdown products and/or deleterious effects of an inflammatory response.

In addition to therapeutic applications, it is intended that non-therapeutic, non-human and industrial applications be included within the scope of the present invention. Cosmetic applications, diagnostic applications and veterinary applications are also contemplated. Repeatedly practicing the method according to the present invention at a low level can be coupled with monitoring to determine the degree of improvement as a diagnostic measure of the component of a condition due to damaged cells versus genetic factors. With respect to tissue and cell culture applications, for example, destruction of blocking cells can permit the resulting dead cells and debris to be washed away. In this way, productivity of cell and tissue cultures can be increased by increasing the relative proportion of productive cells versus non-productive cells.

EXAMPLES

The following examples are for illustrative purposes only and should not be interpreted as limitations of the claimed invention. There are a variety of alternative techniques and procedures available to those of skill in the art that would similarly permit one to successfully perform the intended invention.

Example 1

In an embodiment of the present invention glycation end-products, crosslinks created by sugars bonded to proteins, are selected as indicia of an accumulation of cellular damage correlated with partial- or non-functionality. Antibodies against such glycation end-products can be raised according to methods well known to those skilled in the art (e.g. Abed et al., U.S. Pat. No. 6,380,165; Bucala, U.S. Pat. No. 5,702,704) and humanized monoclonal antibodies retaining constant regions which permit destruction of targeted cells by the immune system can be produced for injection, also according to well known methods (e.g. Basi et al., U.S. Pat. No. 7,256,273). Antibodies can be screened for effectiveness according to the present invention by labeling them and applying them separately to untreated cells versus cells incubated with a sugar such as ribose used to induce formation of glycation end-products. Binding of the antibodies to a higher degree to the cells previously incubated with sugar as opposed to the cells not treated with sugar indicates preferential effect against the selected target.

Antibodies produced as described above can be administered to a subject intravenously with monitoring to determine that inflammatory responses such as fever or swelling do not exceed limits well known to be safe. This process can be repeated at intervals to maintain a level of regeneration. The process can be focused to remove partially- and/or non-functional cells a particular location (e.g. where stem cell transplantation is targeted).

Evaluation of improvement or maintenance of a desired result can be used to direct the frequency of reapplication of the antibodies according to the present invention. The application and reapplication can be determined with the goal of gradual improvement to avoid overwhelming natural mechanisms, such as removal of cells/debris by scavenging cells.

Example 2

In another embodiment of the present invention, glycation end-products, crosslinks created by sugars bonded to proteins, are selected as indicia of an accumulation of cellular damage correlated with partial- or non-functionality. This crosslinking manifests itself in a stiffening of the cells. Those in the art understand stiffness to distinguish types of proliferating versus non-proliferating cells (e.g. Kas et al., U.S. Pat. No. 6,067,859).

Ultrasound apparatus can be used according to practices well known to those skilled in the art to destroy cells by vibrational techniques (e.g. Chapelon et al., U.S. Pat. No. 5,601,526). Ultrasound parameters (e.g. frequency, power, and pulsation) can be screened for effectiveness in selectively destroying stiffer cells according to the present invention by application to untreated cells versus cells incubated with a sugar such as ribose used to induce formation of glycation end-products. Vibrational versus thermal destruction by ultrasound is preferred according to the present invention. Parameters selected for preferential destruction of sugar-treated cells as opposed to the cells not previously treated with sugar indicates preferential effect against the selected target.

Ultrasound as described above can be applied to a subject with monitoring to determine that inflammatory responses such as fever or swelling do not exceed limits well known to be safe. This process can be repeated at intervals to maintain a level of regeneration. The process can be focused to remove partially- and/or non-functional cells a particular location (e.g. where stem cell transplantation is targeted).

Evaluation of improvement or maintenance of a desired result can be used to direct the frequency of reapplication of ultrasound according to the present invention. The application and reapplication can be determined with the goal of gradual improvement to avoid overwhelming natural mechanisms, such as removal of cells/debris by scavenging cells.

While the present invention has been described in terms of preferred embodiments, it is not intended that the present invention be limited to the embodiments described herein, but, rather, that the present invention include all embodiments within the scope of the appended claims as properly construed.

What is claimed is:

1. A method of promoting tissue or organ regeneration in a subject by killing senescent cells comprising a glycation end-product, the method comprising:
   administering to the subject a humanized antibody that binds to the glycation end-product of a cell,
   evaluating the subject to determine if senescent cells have been killed, and
   readministering the antibody, if necessary,
   wherein the subject is human, and
   the humanized antibody retains constant regions which permit destruction of the cells by the subject's immune system.

2. The method of claim 1, wherein the antibody is monoclonal.

3. The method of claim 2, wherein the antibody is conjugated to a toxin.

4. The method of claim 1, wherein the antibody is conjugated to a toxin.

5. A method of promoting regenerative processes or for overcoming aging effects in a subject, the method comprising:
   administering to the subject a humanized antibody that binds to a glycation end-product of a cell,
   evaluating the subject to determine if senescent cells have been killed, and
   readministering the antibody, if necessary,
   wherein the antibody selectively kills senescent cells,
   the subject is human, and
   the humanized antibody retains constant regions which permit destruction of the cells by the subject's immune system.

6. The method of claim 5, wherein the antibody is monoclonal.

7. The method of claim 6, wherein the antibody is conjugated to a toxin.

8. The method of claim 5, wherein the antibody is conjugated to a toxin.

9. A method of selectively killing senescent cells in a subject, the method comprising:
   administering to the subject a humanized antibody that binds to a glycation end-product of a cell,
   evaluating the subject to determine if senescent cells have been killed, and
   readministering the antibody, if necessary,
   wherein the subject is human, and
   the humanized antibody retains constant regions which permit destruction of the cells by the subject's immune system.

10. The method of claim 9, wherein the antibody is monoclonal.

11. The method of claim 10, wherein the antibody is conjugated to a toxin.

12. The method of claim 11, wherein the antibody is conjugated to a toxin.

* * * * *

UNITED STATES PATENT AND TRADEMARK OFFICE
CERTIFICATE OF CORRECTION

PATENT NO.        : 9,161,810 B2
APPLICATION NO.   : 13/332976
DATED             : October 20, 2015
INVENTOR(S)       : Lewis Gruber It is certified that error appears in the above-identified patent and that said Letters Patent is hereby corrected as shown below:

On the Title Page:

Page 2. Item (56) References Cited

Column 1, line 46, please delete "erthrophagocytosis" and insert --erythrophagocytosis--

Column 1, line 47, please delete "erthrocytes" and insert --erythrocytes--

Column 1, line 61, please delete "Fs7 ... 49" and insert --Fs7__49--

Column 2, line 46, please delete "Arthristis" and insert --Arthritis--

Column 2, line 49, please delete "y:" and insert --γ:--

Page 3. Item (56) References Cited

Column 2, line 12, please delete "Experimantal" and insert --Experimental--

Page 4. Item (56) References Cited

Column 1, line 46, please delete "PPAP-y" and insert --PPAR-γ--

Column 2, line 4, please delete "Ibeta" and insert --1beta--

Column 2, line 7, please delete "tubercolosis" and insert --tuberculosis--

Column 2, line 30, please delete "Arterioscerosis" and insert --Arteriosclerosis--

Page 5. Item (56) References Cited

Column 1, line 39, please delete "interferon-y" and insert --interferon-γ--

Column 2, line 33, please delete "wwwv." and insert --www.--

In the Claims:

Column 8, line 20, please delete "The method of claim 11," and insert --The method of claim 9,--

Signed and Sealed this
Twelfth Day of July, 2016

Michelle K. Lee
*Director of the United States Patent and Trademark Office*